United States Patent [19]

Western et al.

[11] Patent Number: 5,792,614
[45] Date of Patent: Aug. 11, 1998

[54] DETECTION OF NUCLEIC ACIDS BY TARGET-CATALYZED PRODUCT FORMATION

[75] Inventors: Linda M. Western, San Mateo; Samuel J. Rose, Los Altos; Edwin F. Ullman, Atherton, all of Calif.

[73] Assignee: Dade Behring Marburg GmbH, Deerfield, Ill.

[21] Appl. No.: 691,627

[22] Filed: Aug. 2, 1996

Related U.S. Application Data

[63] Continuation of Ser. No. 363,169, Dec. 23, 1994, abandoned.

[51] Int. Cl.$^6$ ............................ C12Q 1/68; C12P 19/34; C12N 9/12; C12N 9/14
[52] U.S. Cl. ................... 435/6; 435/91.5; 435/194; 435/195; 435/15; 435/18; 435/91.53; 935/77; 935/78
[58] Field of Search .................... 435/6, 18, 91.53, 435/15, 91.5, 194, 195; 536/24.3; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 4,800,159 | 1/1989 | Mullis et al. | 435/172.3 |
| 4,965,188 | 10/1990 | Mullis et al. | 435/16 |
| 5,008,182 | 4/1991 | Sninsky et al. | 435/5 |
| 5,011,769 | 4/1991 | Duck et al. | 435/6 |
| 5,210,015 | 5/1993 | Gelfand et al. | 435/6 |
| 5,422,253 | 6/1995 | Dahlberg et al. | 435/91.53 |
| 5,487,972 | 1/1996 | Gelfand et al. | 435/6 |

FOREIGN PATENT DOCUMENTS

| | | |
|---|---|---|
| 0 439 182 A2 | 3/1992 | European Pat. Off. . |
| 0 473 155 A2 | 3/1992 | European Pat. Off. . |
| 0 578 138 | 1/1994 | European Pat. Off. . |
| 0 601 834 A1 | 6/1994 | European Pat. Off. . |
| WO 89/09284 | 10/1989 | WIPO . |
| WO 89/10415 | 11/1989 | WIPO . |
| WO89/10415 | 11/1989 | WIPO . |
| WO 91/17264 | 11/1991 | WIPO . |
| WO 92/02638 | 2/1992 | WIPO . |

OTHER PUBLICATIONS

Longley, et al., Nucleic Acids Research, vol. 18:24, (1990) pp. 7317–7322 "Characterization of the 5' to 3' exonuclease associated with Thermus aquaticus DNA ploymerase".

Holland, et al., Proc. Natl. Acad. Sci. USA, vol. 88: (Aug. 1991) pp. 7276–7280 "Detection of specific polymerase chain reaction product by utilizing the 5' to 3' exonuclease activity of Thermus aquaticus".

Lyamichev, et al., Science, vol. 260: (May 7, 1993) pp. 778–783 "Structure-Specific Endonucleolytic Cleavage of Nucleic Acids by Eubacterial DNA Polymerases".

(List continued on next page.)

*Primary Examiner*—Stephanie W. Zitomer
*Attorney, Agent, or Firm*—Theodore J. Leitereg; David M. Maiorana

[57] ABSTRACT

A method is disclosed for modifying an oligonucleotide, which method has application to the detection of a polynucleotide analyte. An oligonucleotide is reversibly hybridized with a polynucleotide, for example, a polynucleotide analyte, in the presence of a 5'-nuclease under isothermal conditions. The polynucleotide analyte serves as a recognition element to enable a 5'-nuclease to cleave the oligonucleotide to provide (i) a first fragment that is substantially non-hybridizable to the polynucleotide analyte and (ii) a second fragment that lies 3' of the first fragment (in the intact oligonucleotide) and is substantially hybridizable to the polynucleotide analyte. At least a 100-fold molar excess of the first fragment and/or the second fragment are obtained relative to the molar amount of the polynucleotide analyte. The presence of the first fragment and/or the second fragment is detected, the presence thereof indicating the presence of the polynucleotide analyte. The method has particular application to the detection of a polynucleotide analyte such as DNA. Kits for conducting methods in accordance with the present invention are also disclosed.

26 Claims, 2 Drawing Sheets

OTHER PUBLICATIONS

Saiki, et al., Science, vol. 239 (Jan. 1988) pp. 487–491 "Primer–Directed Enzymatic Amplification of DNA with a Thermostable DNA Polymerase".

Saiki, et al., Science, vol. 230 (Dec. 1985), pp. 1350–1354 "Enzymatic Amplification of β–Globin Genomic Sequences and Restriction Site Analysis for Diagnosis of Sickle Cell Anemia".

Van Brunt, Bio/Technology, vol. 8 (Apr. 1990), pp. 291–294 "Amplifying Genes: PCR and Its Alternatives".

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:1:

CGTGGGAACA AACGGCGGAT                                                    20

(2) INFORMATION FOR SEQ ID NO:2:

(i) SEQUENCE CHARACTERISTICS:
        (A) LENGTH: 45 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(v) FRAGMENT TYPE: internal

(xi) SEQUENCE DESCRIPTION: SEQ ID NO:2:

TTCATCAACA TTAAATGTGA GCGAGTAACA ACCCGTCGGA TTCTC                        45

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(v) FRAGMENT TYPE: internal

(xi) SEQUENCE DESCRIPTION: SEQ ID NO:3:

TCGTGGGAAC AAACGGCGGA T                                                  21

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(v) FRAGMENT TYPE: internal

(xi) SEQUENCE DESCRIPTION: SEQ ID NO:4:

TTATTTCGTG GGAACAAACG GCGGAT                                             26

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single

```
            ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

GATTAGGATT   AGGATTAGTC   GTGGGAACAA   ACGGCGGAT                            3 9

( 2 ) INFORMATION FOR SEQ ID NO:6:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

GATTAGGATT   AGGATTAGTC                                                     2 0
```

DETECTION OF NUCLEIC ACIDS BY TARGET-CATALYZED PRODUCT FORMATION

This application is a continuation of U.S. patent application Ser. No. 08/268,169 filed Dec. 23, 1994, now abandoned.

BACKGROUND OF THE INVENTION

1. Field of the Invention.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 polynucleotide kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Current methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting nucleic acid sequences is therefore desirable.

Recently, a method for the enzymatic amplification of specific segments of DNA known as the polymerase chain reaction (PCR) method has been described. This in vitro amplification procedure uses two or more different oligonucleotide primers for different strands of the target nucleic acid and is based on repeated cycles of denaturation, oligonucleotide primer annealing, and primer extension by thermophilic polymerase, resulting in the exponential increase in copies of the region flanked by the primers. The different PCR primers, which anneal to opposite strands of the DNA, are positioned so that the polymerase catalyzed extension product of one primer can serve as a template strand for the other primer, leading to the accumulation of discrete fragments whose length is defined by the distance between the 5'-ends of the oligonucleotide primers.

Other methods for amplifying nucleic acids are single primer amplification, ligase chain reaction (LCR), nucleic acid sequence based amplification (NASBA) and the Q-beta-replicase method. Regardless of the amplification used, the amplified product must be detected.

Depending on which of the above amplification methods are employed, the methods generally employ from seven to twelve or more reagents. Furthermore, the above methods provide for exponential amplification of a target or a reporter oligonucleotide. Accordingly, it is necessary to rigorously avoid contamination of assay solutions by the amplified products to avoid false positives. Some of the above methods require expensive thermal cycling instrumentation and additional reagents and sample handling steps are needed for detection of the amplified product.

Most assay methods that do not incorporate amplification of a target DNA avoid the problem of contamination, but they are not adequately sensitive or simple. Some of the methods involve some type of size discrimination such as electrophoresis, which adds to the complexity of the methods.

One method for detecting nucleic acids is to employ nucleic acid probes. One method utilizing such probes is described in U.S. Pat. No. 4,868,104, the disclosure of which is incorporated herein by reference. A nucleic acid probe may be, or may be capable of being, labeled with a reporter group or may be, or may be capable of becoming, bound to a support.

Detection of signal depends upon the nature of the label or reporter group. If the label or reporter group is an enzyme, additional members of the signal producing system include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule, the medium can be irradiated and the fluorescence determined. Where the label is a radioactive group, the medium can be counted to determine the radioactive count.

It is desirable to have a sensitive, simple method for detecting nucleic acids. The method should minimize the number and complexity of steps and reagents. The need for sterilization and other steps needed to prevent contamination of assay mixtures should be avoided.

2. Description of the Related Art.

Methods for detecting nucleic acid sequences are discussed by Duck, et al., in U.S. Pat. No. 5,011,769 and corresponding International Patent Application WO 89/10415. A method of cleaving a nucleic acid molecule is disclosed in European Patent Application 0 601 834 A1 (Dahlberg, et al.).

Holland, et al., Clinical Chemistry (1992) 38:462–463, describe detection of specific polymerase chain reaction product by utilizing the 5' to 3' exonuclease activity of Thermus aquaticus DNA polymerase. Longley, et al., Nucleic Acids Research (1990) 18:7317–7322, discuss characterization of the 5' to 3' exonuclease associated with Thermus aquaticus DNA polymerase. Lyamichev, et al., Science (1993) 260:778–783, disclose structure-specific endonucleolytic cleavage of nucleic acids by eubacterial DNA polymerases.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science*, 230: 1350–1354. Primer-directed enzymatic amplification of DNA with a thermostable DNA polymerase is described by Saiki, et al., *Science* (1988) 239:487.

U.S. patent applications Ser. Nos. 07/299,282 and 07/399,795, filed Jan. 19, 1989, and Aug. 29, 1989, respectively, describe nucleic acid amplification using a single polynucleotide primer. The disclosures of these applications are incorporated herein by reference including the references listed in the sections entitled "Description of the Related Art."

Other methods of achieving the result of a nucleic acid amplification are described by Van Brunt in *Bio/Technology* (1990) 8 (No.4): 291–294. These methods include ligase chain reaction (LCR), nucleic acid sequence based amplification (NASBA) and Q-beta-replicase amplification of RNA. LCR is also discussed in European Patent Applications Nos. 439,182 (Backman I) and 473,155 (Backman II).

NASBA is a promoter-directed, isothermal enzymatic process that induces in vitro continuous, homogeneous and isothermal amplification of specific nucleic acid.

Q-beta-replicase relies on the ability of Q-beta-replicase to amplify its RNA substrate exponentially under isothermal conditions.

Another method for conducting an amplification of nucleic acids is referred to as strand displacement amplification (SDA). SDA is an isothermal, In vitro DNA amplification technique based on the ability of a restriction enzyme to nick the unmodified strand of a hemiphosphorothioate form of its restriction site and the ability of a DNA polymerase to initiate replication at the nick and displace the downstream nontemplate strand intact. Primers containing the recognition sites for the nicking restriction enzyme drive the exponential amplification.

Another amplification procedure for amplifying nucleic acids is known as 3SR, which is an RNA specific target method whereby RNA is amplified in an isothermal process combining promoter directed RNA polymerase, reverse transcriptase and RNase H with target RNA.

SUMMARY OF THE INVENTION

One aspect of the present invention is a method for modifying an oligonucleotide. The method comprises incubating the oligonucleotide with a polynucleotide and a 5'-nuclease wherein at least a portion of the oligonucleotide is reversibly hybridized to the polynucleotide under isothermal conditions. The oligonucleotide is cleaved to provide (i) a first fragment that is substantially non-hybridizable to the polynucleotide and includes no more than one nucleotide from the 5'-end of the portion and (ii) a second fragment that is 3' of the first fragment with reference to the intact oligonucleotide and is substantially hybridizable to the polynucleotide.

Another aspect of the present invention is a method for detecting a polynucleotide analyte. An oligonucleotide is reversibly hybridized with a polynucleotide analyte and a 5'-nuclease under isothermal conditions. The polynucleotide analyte serves as a recognition element to enable a 5'-nuclease to cleave the oligonucleotide to provide (i) a first fragment that is substantially non-hybridizable to the polynucleotide analyte and (ii) a second fragment that lies 3' of the first fragment (in the intact oligonucleotide) and is substantially hybridizable to the polynucleotide analyte. At least a 100-fold molar excess of the first fragment and/or the second fragment are obtained relative to the molar amount of the polynucleotide analyte. The presence of the first fragment and/or the second fragment is detected, the presence thereof indicating the presence of the polynucleotide analyte.

Another embodiment of the present invention is a method for detecting a polynucleotide analyte. A combination is provided comprising a medium suspected of containing the polynucleotide analyte, an excess, relative to the suspected concentration of the polynucleotide analyte, of a first oligonucleotide at least a portion of which is capable of reversibly hybridizing with the polynucleotide analyte under isothermal conditions, a 5'-nuclease, and a second oligonucleotide having the characteristic of hybridizing to a site on the polynucleotide analyte that is 3' of the site at which the first oligonucleotide hybridizes. The polynucleotide analyte is substantially fully hybridized to the second oligonucleotide under such isothermal conditions. The polynucleotide is reversibly hybridized under the isothermal conditions to the first oligonucleotide, which is cleaved as a function of the presence of the polynucleotide analyte to provide, in at least a 100-fold molar excess of the polynucleotide analyte, (i) a first fragment that is substantially non-hybridizable to the polynucleotide analyte and/or (ii) a second fragment that lies 3' of the first fragment (in the intact first oligonucleotide) and is substantially hybridizable to the polynucleotide analyte. The presence of the first fragment and/or the second fragment is detected, the presence thereof indicating the presence of the polynucleotide analyte.

Another embodiment of the present invention is a method for detecting a DNA analyte. A combination is provided comprising a medium suspected of containing the DNA analyte, a first oligonucleotide at least a portion of which is capable of reversibly hybridizing with the DNA analyte under isothermal conditions, a 5'-nuclease, and a second oligonucleotide having the characteristic of hybridizing to a site on the DNA analyte that is 3' of the site at which the first oligonucleotide hybridizes. The DNA analyte is substantially fully hybridized to the second oligonucleotide under isothermal conditions. The polynucleotide analyte is reversibly hybridized to the first oligonucleotide under isothermal conditions. The first oligonucleotide is cleaved to (i) a first fragment that is substantially non-hybridizable to the DNA analyte and (ii) a second fragment that lies 3' of the first fragment (in the intact first oligonucleotide) and is substantially hybridizable to the DNA analyte. At least a 100-fold molar excess, relative to the DNA analyte, of the first fragment and/or the second fragment is produced. The presence of the first fragment and/or the second fragment is detected, the presence thereof indicating the presence of the DNA analyte.

Another embodiment of the present invention is a kit for detection of a polynucleotide. The kit comprises in packaged combination (a) a first oligonucleotide having the characteristic that, when reversibly hybridized under isothermal conditions to the polynucleotide, it is degraded by a 5'-nuclease to provide (i) a first fragment that is substantially non-hybridizable to the polynucleotide and (ii) a second fragment that is 3' of the first fragment (in the first oligonucleotide) and is substantially hybridizable to the polynucleotide, (b) a second oligonucleotide having the characteristic of hybridizing to a site on the polynucleotide that is separated by no more than one nucleotide from the 3'-end of the site at which the first oligonucleotide hybridizes wherein the polynucleotide is substantially fully hybridized to the second oligonucleotide under the isothermal conditions, and (c) a 5'-nuclease.

DESCRIPTION OF THE SPECIFIC EMBODIMENTS

The present invention permits catalyzed cleavage of an oligonucleotide that is modulated by a portion of a polynucleotide analyte, such as a polynucleotide, that is comprised of a target polynucleotide sequence to which a portion of the oligonucleotide hybridizes. As such, the methods of the present invention provide for very high sensitivity assays for polynucleotide analytes. The methods are simple to conduct and no temperature cycling is required. Consequently, no expensive thermal cycling instrumentation is needed. Furthermore, only a few reagents are used, thus further minimizing cost and complexity of an assay. In addition, the absence of amplified products, which are potential amplification targets, permits the use of less rigorous means to avoid contamination of assay solutions by target sequences that could produce false positives.

Before proceeding further with a description of the specific embodiments of the present invention, a number of terms will be defined.

Polynucleotide analyte—a compound or composition to be measured that is a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. Isolation of analytes from the natural state, particularly those having a large number of nucleotides, frequently results in fragmentation. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. Preferred polynucleotide analytes are double stranded DNA (dsDNA) and single stranded DNA (ssDNA). The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

Microorganisms of interest include:

Corynebacteria

*Corynebacterium diphtheria*
Pneumococci

*Diplococcus pneumoniae*
Streptococci

*Streptococcus pyrogenes*
*Streptococcus salivarus*

TABLE I-continued

| Microorganisms of interest include: | |
|---|---|
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The colliform |
| *Klebsiella pneumoniae* | bacteria |
| *Salmonella typhosa* | |
| *Salmonella choleraesuis* | The Salmonellae |
| *Salmonella typhimurium* | |
| *Shigella dysenteria* | |
| *Shigella schmitzii* | |
| *Shigella arabinotarda* | |
| | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |
| Hemophilus-Bordetella group | *Rhizopus oryzae* |
| *Hemophilus influenza, H. duczyi* | *Rhizopus arrhizua* |
| | Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecacea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | Trichophyton mentagrophytes |
| *Bacillus megaterium* | *Keratinomyces ajelloi* |
| *Bacillus cereus* | *Microsporum canis* |
| Anaerobic Soore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shingles) |
| *Clostridium bifermentans* | Virus B |
| *Clostridium sporogenes* | Cytomegalovirus |
| Mycobacteria | Pox Viruses |
| *Mycobacterium tuberculosis hominis* | Variola (smallpox) |
| *Mycobacterium bovis* | Vaccinia |
| *Mycobacterium avium* | Poxvirus bovis |
| *Mycobacterium leprae* | Paravaccinia |
| *Mycobacterium paratuberculosis* | Molluscum contagiosum |

TABLE I-continued

Microorganisms of interest include:

| Actinomycetes (fungus-like bacteria) | Picornaviruses |
|---|---|
| *Actinomyces Isaeli* | Poliovirus |
| *Actinomyces bovis* | Coxsackievirus |
| *Actinomyces naeslundii* | Echoviruses |
| *Nocardia asteraides* | Rhinoviruses |
| *Nocardia brasiliensis* | Myxoviruses |
| The Spirochetes | Influenza (A, B, and C) |
| *Treponema pallidum* Spirillum minus | Parainfluenza (1-4) |
| *Treponema pertenue* Streptobacillus | Mumps Virus |
| *monoiliformis* | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplassa pneumoniae* | |
| Other pathogens | Eastern Equine Encephalitis Virus |
| *Listeria monocytogenes* | Western Equine Encephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1-3 Retroviruses |
| *Rickettsia akari* | Human Immunodeficiency Viruses |
| (HIV) | |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis nonA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |
| *Aspergillus fumigatus* | |
| *Mucor corymbifer* (*Absidia corymbifera*) | |

The polynucleotide analyte, where appropriate, may be treated to cleave the analyte to obtain a polynucleotide that contains a target polynucleotide sequence, for example, by shearing or by treatment with a restriction endonuclease or other site specific chemical cleavage method. However, it is an advantage of the present invention that the polynucleotide analyte can be used in its isolated state without further cleavage.

For purposes of this invention, the polynucleotide analyte, or a cleaved polynucleotide obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90°–100° C. for a period of about 1 to 10 minutes to produce denatured material. 3'- or 5'-End of an oligonucleotide—as used herein this phrase refers to a portion of an oligonucleotide comprising the 3'- or 5'-terminus, respectively, of the oligonucleotide.

3'- or 5'-Terminus of an oligonucleotide—as used herein this term refers to the terminal nucleotide at the 3'- or 5'-end, respectively, of an oligonucleotide.

Target polynucleotide sequence—a sequence of nucleotides to be identified, which may be the polynucleotide analyte but is usually existing within a polynucleotide comprising the polynucleotide analyte. The identity of the target polynucleotide sequence is known to an extent sufficient to allow preparation of an oligonucleotide having a portion or sequence that hybridizes with the target polynucleotide sequence. In general, when one oligonucleotide is used, the oligonucleotide hybridizes with the 5'-end of the target polynucleotide sequence. When a second oligonucleotide is used, it hybridizes to a site on the target polynucleotide sequence that is 3' of the site to which the first oligonucleotide hybridizes. (It should be noted that the relationship can be considered with respect to the double stranded molecule formed when the first and second oligonucleotides are hybridized to the polynucleotide. In such context the second oligonucleotide is 5-primeward of the first oligonucleotide with respect to the "strand" comprising the first and second oligonucleotides.) The relationships described above are more clearly seen with reference to FIG. 3. The target polynucleotide sequence usually contains from about 10 to 1,000 nucleotides, preferably 15 to 100 nucleotides, more preferably, 20 to 70 nucleotides. The target polynucleotide sequence is part of a polynucleotide that may be the entire polynucleotide analyte. The minimum number of nucleotides in the target polynucleotide sequence is selected to assure that the presence of target polynucleotide sequence in a sample is a specific indicator of the presence of polynucleotide analyte in a sample. Very roughly, the sequence length is usually greater than about 1.6 log L nucleotides where L is the number of base pairs in the genome of the biologic source of the sample. The number of nucleotides in the target sequence is usually the sum of the lengths of those portions of the oligonucleotides that hybridize with the target sequence plus the number of nucleotides lying between the portions of the target sequence that hybridize with the oligonucleotides.

Oligonucleotide—a polynucleotide, usually a synthetic polynucleotide, usually single stranded that is constructed such that at least a portion thereof hybridizes with the target polynucleotide sequence of the polynucleotide. The oligonucleotides of this invention are usually 10 to 150 nucleotides, preferably, deoxyoligonucleotides of 15 to 100 nucleotides, more preferably, 20 to 60 nucleotides, in length.

The first oligonucleotide, or "the" oligonucleotide when a second oligonucleotide is not employed, has a 5'-end about 0 to 100 nucleotides, preferably, 1 to 20 nucleotides in length that does not hybridize with the target polynucleotide sequence and usually has a 10 to 40 nucleotide sequence that hybridizes with the target polynucleotide sequence. In general, the degree of amplification is reduced somewhat as the length of the portion of the oligonucleotide that does not hybridize with the target polynucleotide sequence increases.

The first oligonucleotide also may have a sequence at its 3'-end that does not hybridize with the target polynucleotide sequence.

The second oligonucleotide preferably hybridizes at its 3'-end with the target polynucleotide sequence at a site on the target polynucleotide sequence 3' of the site of binding of the first oligonucleotide. The length of the portion of the second oligonucleotide that hybridizes with the target polynucleotide sequence is usually longer than the length of the portion of the first oligonucleotide that hybridizes with the target polynucleotide sequence and is usually 20 to 100 nucleotides. The melting temperature of the second oligonucleotide hybridized to the target polynucleotide sequence is preferably at least as high, more preferably, at least 5° C. higher than the melting temperature of the first oligonucleotide hybridized to the target polynucleotide sequence.

The oligonucleotides can be oligonucleotide mimics such a polynucleopeptides, phosphorothioates or phosphonates except that the first oligonucleotide usually has at least one phosphodiester bond to the nucleoside at the 5'-end of the sequence that hybridizes with the target polynucleotide sequence. When oligonucleotide mimics are used that provide very strong binding, such as polynucleopeptides, the length of the portion of the second oligonucleotide that hybridizes with the target polynucleotide sequence may be reduced to less than 20 and, preferably, greater than 10.

Various techniques can be employed for preparing an oligonucleotide or other polynucleotide utilized in the present invention. They can be obtained by biological synthesis or by chemical synthesis. For short oligonucleotides (up to about 100 nucleotides) chemical synthesis will frequently be more economical as compared to biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide sequence. The oligonucleotides can be synthesized by standard methods such as those used in commercial automated nucleic acid synthesizers. Chemical synthesis of DNA on a suitably modified glass or resin results in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol.* 101, 20–78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., *Meth. Enzymol* (1979) 68: 90) and synthesis on a support (Beaucage, et al., *Tetrahedron* (1981) *Letters* 22: 1859–1862) as well as phosphoramidate techniques, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Fragment—in general, in the present method the oligonucleotide (or the first oligonucleotide when a second oligonucleotide is employed) is cleaved only when at least a portion thereof is reversibly hybridized with a target polynucleotide sequence and, thus, the target polynucleotide sequence acts as a recognition element for cleavage of the oligonucleotide, thereby yielding two portions. One fragment is substantially non-hybridizable to the target polynucleotide sequence. The other fragment is substantially hybridizable to the target polynucleotide sequence and 3' of the other fragment with respect to the oligonucleotide in its uncleaved form.

5'-Nuclease—a sequence-independent deoxyribonuclease enzyme that catalyzes the cleavage of an oligonucleotide into fragments only when at least a portion of the oligonucleotide is hybridized to the target polynucleotide sequence. The enzyme selectively cleaves the oligonucleotide near the 5'-terminus of the bound portion, within 5 nucleotides thereof, preferably within 1 to 2 nucleotides thereof and does not cleave the unhybridized oligonucleotide or the target polynucleotide sequence. Such enzymes include both 5'-exonucleases and 5'-endonucleases but exclude ribonucleases such as RNAse H and restriction enzymes. 5'-nucleases useful in the present invention must be stable under the isothermal conditions used in the present method and are usually thermally stable nucleotide polymerases having 5'-exonuclease activity such as Taq DNA polymerase (e.g. AmpliTaq(TM) from Perkin-Elmer Corporation, Norwalk, N.J.), Thermalase Tbr(TM) DNA polymerase (from Amresco, Solon, Ohio), Ultra Therm(TM) DNA polymerase (from Bio/Can Scientific, Ontario, Canada), Replitherm(TM) DNA polymerase (from Epicentre, Madison, Wis.), Tfl (TM) DNA polymerase (from Epicentre), Panozyme(TM) DNA polymerase (from Panorama Research, Mountain View, Calif.), Tth(TM) DNA polymerase (from Epicentre), rBst(TM) DNA polymerase (from Epicentre), Heat Tuff(TM) DNA polymerase (from Clontech, Palo Alto, Calif.), and the like, derived from any source such as cells, bacteria, such as *E. coli*, plants, animals, virus, thermophilic bacteria, and so forth wherein the polymerase may be modified chemically or through genetic engineering to provide for thermal stability and/or increased activity.

Isothermal conditions—a uniform or constant temperature at which the modification of the oligonucleotide in accordance with the present invention is carried out. The temperature is chosen so that the duplex formed by hybridizing the oligonucleotide to a polynucleotide with a target polynucleotide sequence is in equilibrium with the free or unhybridized oligonucleotide and free or unhybridized target polynucleotide sequence, a condition that is otherwise referred to herein as "reversibly hybridizing" the oligonucleotide with a polynucleotide. Normally, at least 1%, preferably 20 to 80%, usually less than 95% of the polynucleotide is hybridized to the oligonucleotide under the isothermal conditions. Accordingly, under isothermal conditions there are molecules of polynucleotide that are hybridized with the oligonucleotide, or portions thereof, and are in dynamic equilibrium with molecules that are not hybridized with the oligonucleotide. Some fluctuation of the temperature may occur and still achieve the benefits of the present invention. The fluctuation generally is not necessary for carrying out the methods of the present invention and usually offer no substantial improvement. Accordingly, the term "isothermal conditions" includes the use of a fluctuating temperature, particularly random or uncontrolled fluctuations in temperature, but specifically excludes the type of fluctuation in temperature referred to as thermal cycling, which is employed in some known amplification procedures, e.g., polymerase chain reaction.

Polynucleotide primer(s) or oligonucleotide primer(s)—an oligonucleotide that is usually employed in a chain extension on a polynucleotide template.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine(G), inosine, and derivatives and analogs thereof. The pyrimidine bases include cytosine (C), thymine (T), uracil (U), and derivatives and analogs thereof. Nucleoside triphosphates include deoxyribonucleoside triphosphates such as dATP, dCTP, dGTP and dTTP and ribonucleoside triphosphates such as rATP, rCTP, rGTP and rUTP. The term "nucleoside triphosphates" also includes derivatives and analogs thereof.

Nucleotide—a base-sugar-phosphate combination that is the monomeric unit of nucleic acid polymers, i.e., DNA and RNA.

Nucleoside—is a base-sugar combination or a nucleotide lacking a phosphate moiety.

Nucleotide polymerase—a catalyst, usually an enzyme, for forming an extension of an oligonucleotide along a polynucleotide template where the extension is complementary thereto. The nucleotide polymerase is a template dependent polynucleotide polymerase and utilizes nucleoside triphosphates as building blocks for extending the 3'-end of a oligonucleotide to provide a sequence complementary with the single stranded portion of the polynucleotide to which the oligonucleotide is hybridized to form a duplex.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Homologous or substantially identical—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Copy—means a sequence that is a direct identical or homologous copy of a single stranded polynucleotide sequence as differentiated from a sequence that is complementary to the sequence of such single stranded polynucleotide.

Member of a specific binding pair ("sbp member")—one of two different molecules, having an area on the surface or in a cavity which specifically binds to, and is thereby defined as complementary with, a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support or may itself be a label.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label or reporter group or reporter molecule—a member of a signal producing system. Usually the label or reporter group or reporter molecule is conjugated to or becomes bound to, or fragmented from, an oligonucleotide or to a nucleoside triphosphate and is capable of being detected directly or, through a specific binding reaction, and can produce a detectible signal. In general, any label that is detectable can be used. The label can be isotopic or nonisotopic, usually non-isotopic, and can be a catalyst, such as an enzyme or a catalytic polynucleotide, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectible group, and the like.

Labels include an oligonucleotide or specific polynucleotide sequence that can provide a template for amplification or ligation or act as a ligand such as for a repressor protein. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—The signal producing system may have one or more components, at least one component being the label or reporter group or reporter molecule. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to, or part of, a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. The signal-producing system is described more fully in U.S. patent application Ser. No. 07/555,323, filed Jul. 19, 1990, the relevant disclosure of which is incorporated herein by reference.

Amplification of nucleic acids or polynucleotides—any method that results in the formation of one or more copies of a nucleic acid or a polynucleotide molecule, usually a nucleic acid or polynucleotide analyte, or complements thereof, present in a medium.

Exponential amplification of nucleic acids or polynucleotides—any method that results in the formation of one or more copies of a nucleic acid or polynucleotide molecule, usually a nucleic acid or polynucleotide analyte, present in a medium.

Methods for the enzymatic amplification of specific double stranded sequences of DNA include those described above such as the polymerase chain reaction (PCR), amplification of a single stranded polynucleotide using a single polynucleotide primer, ligase chain reaction (LCR), nucleic acid sequence based amplification (NASBA), Q-beta-replicase method, strand displacement amplification (SDA), and 3SR.

Conditions for carrying out an amplification, thus, vary depending upon which method is selected. Some of the methods such as PCR utilize temperature cycling to achieve denaturation of duplexes, oligonucleotide primer annealing, and primer extension by thermophilic template dependent polynucleotide polymerase. Other methods such as NASBA, Q-beta-replicase method, SDA and 3SR are isothermal. As can be seen, there are a variety of known amplification methods and a variety of conditions under which these methods are conducted to achieve exponential amplification.

Linear amplification of nucleic acids or polynucleotides—any method that results in the formation of one or more copies of only the complement of a nucleic acid or polynucleotide molecule, usually a nucleic acid or polynucleotide analyte, present in a medium. Thus, one difference between linear amplification and exponential amplification is that the latter produces copies of the polynucleotide whereas the former produces only the complementary strand of the polynucleotide. In linear amplification the number of complements formed is, in principle, directly proportional to the time of the reaction as opposed to exponential amplification wherein the number of copies is, in principle, an exponential function of the time or the number of temperature cycles.

Ancillary Materials—various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above, the present invention has a primary application to methods for detecting a polynucleotide analyte. In one aspect of the invention an oligonucleotide is reversibly hybridized with a polynucleotide analyte in the presence of a 5'-nuclease under isothermal conditions. In this way the polynucleotide analyte serves as a "recognition element" to enable the 5'-nuclease to specifically cleave the oligonucleotide to provide first and second fragments when the oligonucleotide is reversibly hybridized to the polynucleotide analyte. The first fragment comprises the 5'-end of the oligonucleotide (with reference to the intact or original oligonucleotide) and is substantially non hybridizable to the polynucleotide analyte and can serve as a label. The first fragment generally includes at least a portion of that part the 5'-end of the original oligonucleotide that was not hybridized to the polynucleotide analyte when the portion of the oligonucleotide that is hybridizable with the polynucleotide analyte is reversibly hybridized thereto. Additionally, the first fragment may include nucleotides (usually, no more than 5, preferably, no more than 2, more preferably, no more than 1 of such nucleotides) that are cleaved by the 5'-nuclease from the 5'-end of that portion (or sequence) of the original oligonucleotide that was hybridized to the polynucleotide analyte. Therefore, it is in the above context that the first fragment is "substantially non-hybridizable" with the polynucleotide analyte. The second fragment comprises the sequence of nucleotides at the 3'-end of the oligonucleotide that were reversibly hybridized to the polynucleotide analyte minus those nucleotides cleaved by the 5'-nuclease when the original oligonucleotide is reversibly hybridized to the polynucleotide analyte. Accordingly, the second fragment is "substantially hybridizable" to the polynucleotide analyte having resulted from that portion of the oligonucleotide that reversibly hybridizes with the polynucleotide analyte.

As mentioned above, the 3'-end of the oligonucleotide may include one or more nucleotides that do not hybridize with the polynucleotide analyte and may comprise a label. At least a 100-fold molar excess of the first fragment and/or the second fragment are obtained relative to the molar amount of the polynucleotide analyte. The sequence of at least one of the fragments is substantially preserved during the reaction. The presence of the first fragment and/or the second fragment is detected, the presence thereof indicating the presence of the polynucleotide analyte.

The 5'-nuclease is generally present in an amount sufficient to cause the cleavage of the oligonucleotide, when it is reversibly hybridized to the polynucleotide analyte, to proceed at least half as rapidly as the maximum rate achievable with excess enzyme, preferably, at least 75% of the maximum rate. The concentration of the 5'-nuclease is usually determined empirically. Preferably, a concentration is used that is sufficient such that further increase in the concentration does not decrease the time for the amplification by over 5-fold, preferably 2-fold. The primary limiting factor generally is the cost of the reagent. In this respect, then, the polynucleotide analyte, or at least the target polynucleotide sequence, and the enzyme are generally present in a catalytic amount.

The oligonucleotide that is cleaved by the enzyme is usually in large excess, preferably, $10^{-9}$M to $10^{-5}$M, and is used in an amount that maximizes the overall rate of its cleavage in accordance with the present invention wherein the rate is at least 10%, preferably, 50%, more preferably, 90%, of the maximum rate of reaction possible. Concentrations of the oligonucleotide lower than 50% may be employed to facilitate detection of the fragment(s) produced in accordance with the present invention. The amount of oligonucleotide is at least as great as the number of molecules of product desired. Usually, the concentration of the oligonucleotide is 0.1 nanomolar to 1 millimolar, preferably, 1 nanomolar to 10 micromolar. It should be noted that increasing the concentration of the oligonucleotide causes the reaction rate to approach a limiting value that depends on the oligonucleotide sequence, the temperature, the concentration of the target polynucleotide sequence and the enzyme concentration. For many detection methods very high concentrations of the oligonucleotide may make detection more difficult.

The amount of the target polynucleotide sequence that is to be copied can be as low as one or two molecules in a sample but generally may vary from about $10^2$ to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M.

In carrying out the methods in accordance with the present invention, an aqueous medium is employed. Other polar solvents may also be employed as cosolvents, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and preferably in the range of about 6–8. The pH and temperature are chosen so as to achieve the reversible hybridization or equilibrium state under which cleavage of an oligonucleotide occurs in accordance with the present invention. In some instances, a compromise is made in the reaction parameters in order to optimize the speed, efficiency, and specificity of these steps of the present method. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

As mentioned above the reaction in accordance with the present invention is carried out under isothermal conditions. The reaction is generally carried out at a temperature that is near the melting temperature of the oligonucleotide:polynucleotide analyte complex. Accordingly, the temperature employed depends on a number of factors. Usually, for cleavage of the oligonucleotide in accordance with the present invention, the temperature is about 35° C. to 90° C. depending on the length and sequence of the oligonucleotide. It will usually be desired to use relatively high temperature of 60° C. to 85° C. to provide for a high rate of reaction. The amount of the fragments formed depends on the incubation time and temperature. In general, a moderate temperature is normally employed for carrying out the methods. The exact temperature utilized also varies depending on the salt concentration, pH, solvents used, and the length of and composition of the target polynucleotide sequence as well as the oligonucleotide as mentioned above.

Figure 1:
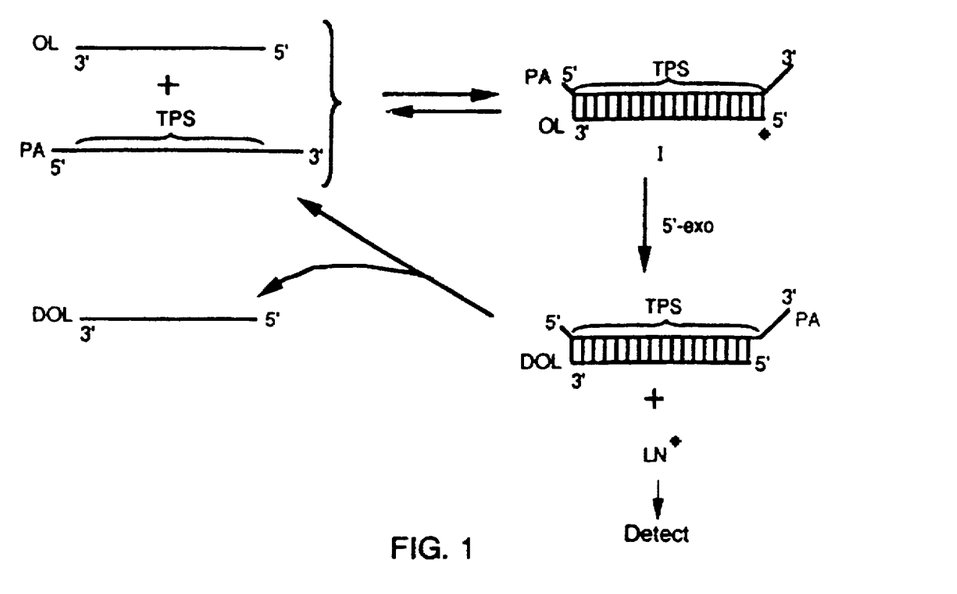
FIGS. 1–3 are schematics of different embodiments in accordance with the present invention.

One embodiment of the invention is depicted in FIG. 1. Oligonucleotide OL is combined with polynucleotide analyte PA having target polynucleotide sequence TPS and with a 5'-nuclease, which can be, for example, a Taq polymerase. In this embodiment OL is labeled (*) within what is designated the first fragment, produced upon cleavage of the oligonucleotide in accordance with the present invention. OL in this embodiment usually is at least 10 nucleotides in length, preferably, about 10 to 50 nucleotides in length, more preferably, 15 to 30 or more nucleotides in length. In general, the length of OL should be sufficient so that a portion hybridizes with TPS, the length of such portion approximating the length of TPS. In this embodiment the length of OL is chosen so that the cleavage of no more than 5, preferably, no more than 1 to 3, more preferably, 1 to 2 nucleotides, therefrom results in two fragments. The first fragment, designated LN, is no more than 5 nucleotides in length, preferably, 1 to 3 nucleotides in length, more preferably, 1 to 2 nucleotides in length and the second fragment, designated DOL, is no more than 5, preferably, no more than 1 to 3, more preferably, no more than 1 to 2, nucleotides shorter than the length of OL.

As shown in FIG. 1, OL hybridizes with TPS to give duplex I. The hybridization is carried out under isothermal conditions so that OL is reversibly hybridized with TPS. OL in duplex I is cleaved to give DOL and LN, wherein LN includes a labeled nucleotide (*) In the embodiment depicted in FIG. 1, DOL is the complement of TPS except for the nucleotides missing at the 5'-end. Since during the course of the isothermal reaction the 5'-end of PA may be cleaved at or near the 5'-end of TPS, DOL may also have 0 to 5 nucleotides at its 3'-end that overhang and cannot hybridize with the residual portion of TPS. The isothermal conditions are chosen such that equilibrium exists between duplex I and its single stranded components, namely, PA and OL. Upon cleavage of OL within duplex I, an equilibrium is also established between duplex I and its single stranded components, PA and DOL. Since OL is normally present in large excess relative to the amount of DOL formed in the reaction, there are usually many more duplexes containing OL than DOL. The reaction described above for duplex I continuously produces additional molecules of DOL.

The reaction is allowed to continue until a sufficient number of molecules of DOL and LN are formed to permit detection of the labeled LN (LN*) and, thus, the polynucleotide analyte. In this way the enzyme-catalyzed cleavage of nucleotides from the 5'-end of OL is modulated by and, therefore, related to the presence of the polynucleotide analyte. Depending on the amount of PA present, a sufficient number of molecules for detection can be obtained where the time of reaction is from about 1 minute to 24 hours. Preferably, the reaction can be carried out in less than 5 hours. As a matter of convenience it is usually desirable to minimize the time period as long as the requisite of number of molecules of detectable fragment is achieved. In general, the time period for a given degree of cleavage can be minimized by optimizing the temperature of the reaction and using concentrations of the 5'-nuclease and the oligonucleotide that provide reaction rates near the maximum achievable with excess of these reagents. Detection of the polynucleotide analyte is accomplished indirectly by detecting the label in fragment LN*. Alternatively, DOL may be detected, for example, by using the label as a means of separating LN* and OL from the reaction mixture and then detecting the residual DOL.

Detection of the labeled fragment is facilitated in a number of ways. For example, a specific pair member such as biotin or a directly detectable label such a fluorescein can be used. The low molecular weight LN* can be separated by electrophoresis, gel exclusion chromatography, thin layer chromatography ultrafiltration and the like and detected by any convenient means such as a competitive binding assay or direct detection of the label. Alternatively, the oligonucleotide can be labeled within the second (DOL) fragment with a specific binding member such as a ligand, a small organic molecule, a polynucleotide sequence or a protein, or with a directly detectable label such as a directly detectable small organic molecules, e.g., fluorescein, a sensitizer, a coenzyme and the like. Detection will then depend on differentiating the oligonucleotide with labels on both ends from singly labeled fragments where one labeled end has been cleaved. In this case it is desirable to label one end of OL with a specific binding member that facilitates removal of OL and the fragment retaining the label by using a complementary sbp member bound to a support. The residual labeled fragments bearing the other label are then detected by using a method appropriate for detecting that label.

One method for detecting nucleic acids is to employ nucleic acid probes. Other assay formats and detection formats are disclosed in U.S. patent applications Ser. Nos. 07/229,282 and 07/399,795 filed Jan. 19, 1989, and Aug. 29, 1989, respectively, U.S. patent application Ser. No. 07/555,323 filed Jul. 19, 1990, U.S. patent application Ser. No. 07/555,968 and U.S. patent application Ser. No. 07/776,538 filed Oct. 11, 1991, which have been incorporated herein by reference.

Examples of particular labels or reporter molecules and their detection can be found in U.S. patent application Ser. No. 07/555,323 filed Jul. 19, 1990, the relevant disclosure of which is incorporated herein by reference.

Detection of the signal will depend upon the nature of the signal producing system utilized. If the label or reporter group is an enzyme, additional members of the signal producing system include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule, the medium can be irradiated and the fluorescence determined. Where the label is a radioactive group, the medium can be counted to determine the radioactive count.

Figure 2:
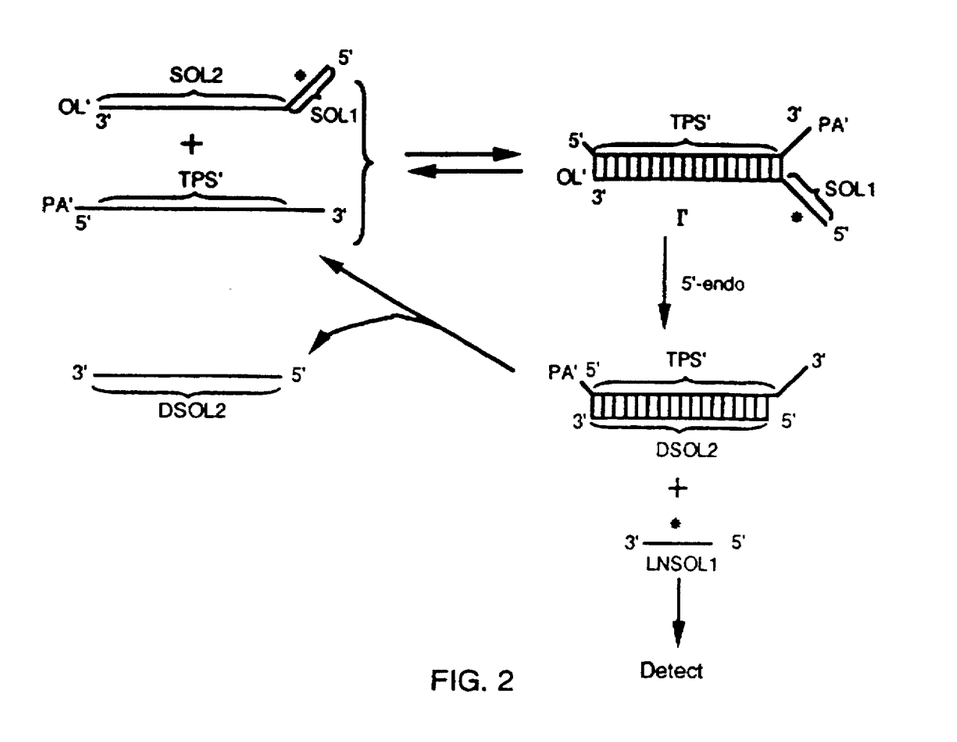

Another embodiment of the present invention is depicted in FIG. 2. Oligonucleotide OL' has a first portion or sequence SOL1 that is not hybridized to TPS' and a second portion or sequence SOL2 that is hybridized to TPS'. OL' is combined with polynucleotide analyte PA' having target polynucleotide sequence TPS' and with a 5'-endonuclease (5'-endo), which can be, for example, Taq DNA polymerase and the like. OL' and 5'-endo are generally present in concentrations as described above. In the embodiment of FIG. 2, OL' is labeled (*) within the sequence SOL1 wherein SOL1 may intrinsically comprise the label or may be extrinsically labeled with a specific binding member or directly detectable labeled. The length of SOL2 is as described in the embodiment of FIG. 1. In general, the length of SOL2 should be sufficient to hybridize with TPS', usually approximating the length of TPS'. SOL1 may be any length as long as it does not substantially interfere with the cleavage of OL' and will preferably be relatively short to avoid such interference. Usually, SOL1 is about 1 to 100 nucleotides in length, preferably, 8 to 20 nucleotides in length.

In this embodiment the cleavage of SOL1 from SOL2 results in two fragments. Cleavage in SOL2 occurs within 5 nucleotides of the bond joining SOL1 and SOL2 in OL'. The exact location of cleavage is not critical so long as the enzyme cleaves OL' only when it is bound to TPS'. The two fragments are designated LNSOL1 and DSOL2. LNSOL1 is comprised of the 5'-end of OL' and DSOL2 is comprised of the 3'-end of OL'. The sequence of at least one of LNSOL1 and DSOL2 remains substantially intact during the cleavage reaction. As shown in FIG. 2, SOL2 of OL' hybridizes with TPS' to give duplex I'. The hybridization is carried out under isothermal conditions so that OL' is reversibly hybridized with TPS'. OL' in duplex I' is cleaved to give DSOL2 and LNSOL1, the latter of which comprises a label. In the embodiment depicted in FIG. 2, DSOL2 is the complement of TPS' except for any nucleotides missing at the 5'-end thereof as a result of the cleavage of the cleavage reaction and any nucleotides appended to the 3'-end of OL' (not shown in FIG. 2) that do not hybridize with TPS'.

The isothermal conditions are chosen such that equilibrium exists between duplex I' and its single stranded components, i.e., PA' and OL'. Upon cleavage of OL' within duplex I' and equilibrium is also established between duplex I' and its single stranded components, PA' and DSOL2. Since OL' is normally present in large excess relative to the amount of DSOL2 formed in the reaction, there are usually many more duplexes containing OL' than DSOL2. The reaction described above for duplex I' continuously produces molecules of DSOL2 and LNSOL1. The reaction is allowed to continue until a sufficient number of molecules of DSOL2 and LNSOL1 are formed to permit detection of one or both of these fragments. In this way the enzyme-catalyzed cleavage of LNSOL1 from the 5'-end of the portion of OL' hybridized to PA', is modulated by, and therefore related to, the presence of the polynucleotide analyte. The reaction parameters and the detection of DSOL2 and/or LNSOL1 are generally as described above for the embodiment of FIG. 1.

Various ways of controlling the cleavage of the oligonucleotide can be employed. For example, the point of cleavage can be controlled by introducing a small organic group, such as biotin, into the nucleotide at the 5'-terminus of OL' or the nucleotide in SOL2 that is at the junction of SOL2 and SOL1.

Figure 3:
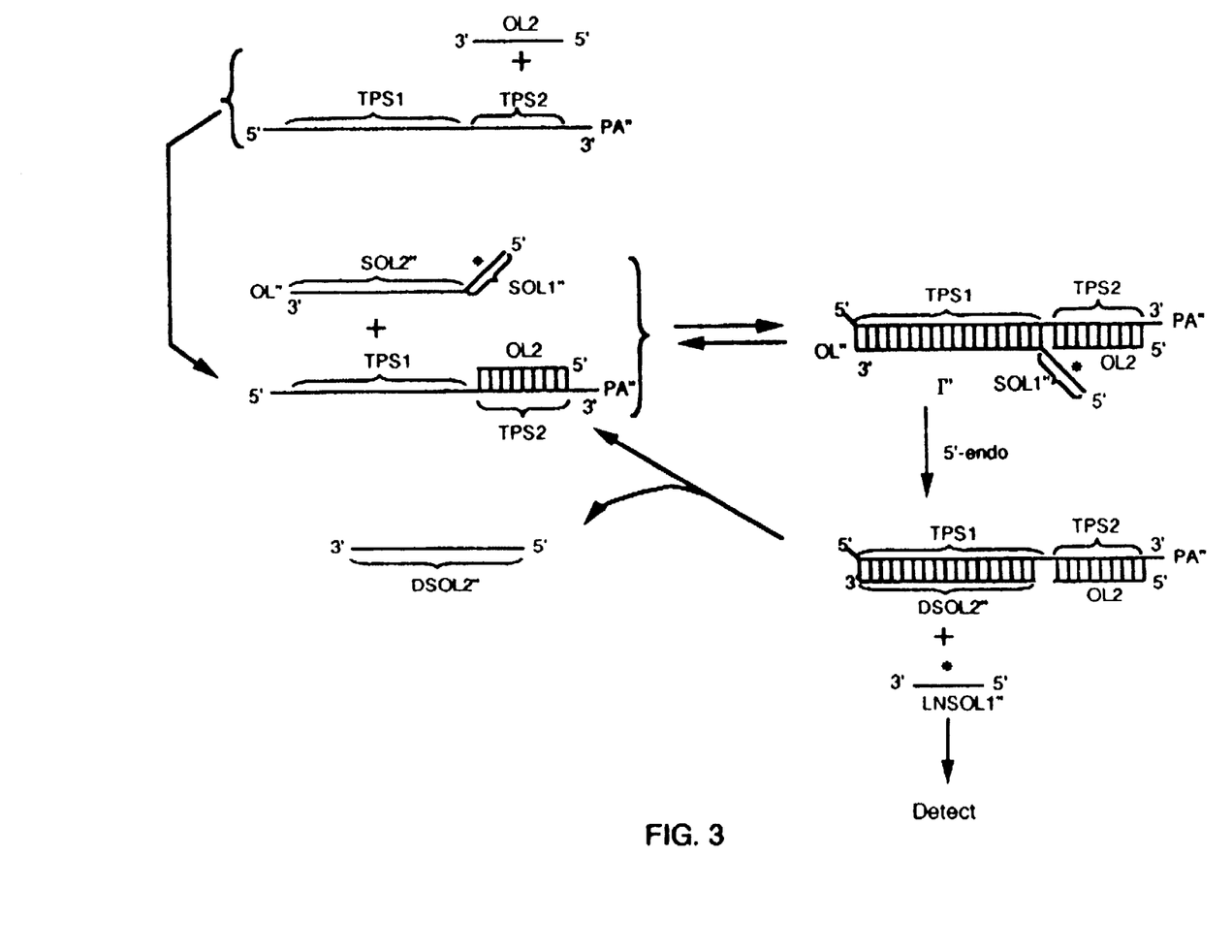

An embodiment using a second oligonucleotide is depicted in FIG. 3. The second oligonucleotide (OL2) hybridizes to a site TPS2 on PA" that lies 3' of the site of hybridization (TPS1) of the sequence SOL2" of the first oligonucleotide, namely, OL'. In the embodiment shown OL2 fully hybridizes with TPS2. This is by way of example and not limitation. The second oligonucleotide can include nucleotides at its 5' end that are not hybridizable with the target polynucleotide sequence, but its 3'-end is preferably hybridizable. Preferably, OL2 binds to a site (TPS2) that is contiguous with the site to which SOL2" hybridizes (TPS1). However, it is within the purview of the present invention that the second oligonucleotide hybridize with PA" within 1 to 5 nucleotides, preferably, 1 nucleotide, of the site to which SOL2" hybridizes. The second oligonucleotide, OL2, is usually at least as long as, and preferably longer than, SOL2", preferably, at least 2 nucleotides longer than SOL2". In general, the second oligonucleotide is about 20–100 nucleotides in length, preferably, 30–80 nucleotides in length depending on the length of SOL2". Normally, the second oligonucleotide is chosen such that it dissociates from duplex I" at a higher temperature than that at which OL" dissociates, usually at least 3° C., preferably, at least 5° C. or more higher.

The presence of OL2 in duplex I" can effect the site of cleavage of OL". In particular, when OL2 binds to PA" that is not contiguous with the SOL2" site of hybridization, the cleavage site may be shifted one or more nucleotides.

The concentration of the second oligonucleotide employed in this embodiment is usually at least 1 picomolar, but is preferably above 0.1 nanomolar to facilitate rapid binding to PA", more preferably, at least 1 nanomolar to 1 micromolar. In accordance with the embodiment of FIG. 3, OL" in duplex I" is cleaved by 5'-endo to give DSOL2" and LNSOL1". The reaction is permitted to continue until the desired number of molecules of labeled fragment are formed. The reaction parameters and detection of DSOL2" and/or LNSOL1" are similar to those described above for the embodiment of FIG. 1.

In general and specifically in any of the embodiments of FIGS. 1 to 3 above, the 3'-end of the first oligonucleotide, for example, OL, OL' and OL", may have one or more nucleotides that do not hybridize with the target polynucleotide sequence and can serve as a label but need not do so.

It is also within the purview of the present invention to employ a single nucleoside triphosphate in any of the above embodiments, depending on the particular 5'-endonuclease chosen for the above cleavage. The decision to use a nucleoside triphosphate and the choice of the nucleoside triphosphate are made empirically based on its ability to accelerate the reaction in accordance with the present invention. The nucleoside triphosphate is preferably one that cannot be incorporated into the first oligonucleotide as a consequence of the binding of the oligonucleotide to the target polynucleotide sequence. In this particular embodiment the added nucleoside triphosphate is present in a concentration of 1 micromolar to 10 millimolar, preferably, 10 micromolar to 1 millimolar, more preferably, 100 micromolar to 1 millimolar. It is also within the purview of the present invention to utilize the added nucleoside triphosphate to chain extend the 3'-terminus of the second oligonucleotide to render it contiguous with the site on the target polynucleotide sequence at which the first oligonucleotide hybridizes. In this approach the second oligonucleotide serves as a polynucleotide primer for chain extension. In addition, the nucleoside triphosphate is appropriately selected to accomplish such chain extension and the 5'-nuclease is selected to also have template-dependent nucleotide polymerase activity. In any event such an approach is primarily applicable to the situation where the site of binding of this second oligonucleotide, TPS2, is separated from the site of binding of the first oligonucleotide, TPS1, by a sequence of one or more identical bases that are complementary to the added nucleotide triphosphate.

In the embodiment of FIG. 3 the mixture containing PA", OL", the second oligonucleotide OL2 and the nucleoside triphosphate is incubated at an appropriate isothermal temperature at which OL" and PA" are in equilibrium with duplex I" wherein most of the molecules of PA" and duplex I" are hybridized to OL2. During the time when a molecule of OL" is bound to PA", the 5'-endo causes the cleavage by hydrolysis of OL" in accordance with the present invention. When the remaining portion of cleaved oligonucleotide (DSOL2") dissociates from PA", an intact molecule of OL" becomes hybridized, whereupon the process is repeated.

In one experiment in accordance with the above embodiment, incubation for 3 hours at 72° C. resulted in the production of over $10^{12}$ molecules of DSOL2" and LNSOL1", which was over $10^4$ increase over the number of molecules of PA" that was present initially in the reaction mixture. OL" was labeled with a $^{32}$P-phosphate at the 5'-terminus. The cleaved product LNSOL1" was detected by applying the mixture to an electrophoresis gel and detecting a band that migrated more rapidly than the band associated with OL". The appearance of this band was shown to be associated with the presence and amount of PA" where a minimum of $10^8$ molecules of PA" was detected.

Alternative approaches for detection of LNSOL1" and/or DSOL2" may also be employed in the above embodiment. For example, in one approach biotin is attached to any part of SOL2" that is cleaved from OL" by the 5'-endonuclease. The fragment DSOL2" and OL" containing the biotin are separated from LNSOL1", for example, by precipitation with streptavidin and filtration. The unprecipitated labeled fragment LNSOL1" is then detected by any standard binding assay, either without separation (homogeneous) or with separation (heterogeneous) of any of the assay components or products.

Homogeneous immunoassays are exemplified by enzyme multiplied immunoassay techniques ("EMIT") disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59 to column 23, line 25; enzyme channeling techniques such as those disclosed in Maggio, et al., U.S. Pat. No. 4,233,402, column 6, line 25 to column 9, line 63; and other enzyme immunoassays such as the enzyme linked immunosorbent assay ("ELISA") are discussed in Maggio, E.T. supra. Exemplary of heterogeneous assays are the radioimmunoassay, disclosed in Yalow, et al., *J. Clin. Invest.* 39:1157 (1960). The above disclosures are all incorporated herein by reference. For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. A typical non-competitive assay is a sandwich assay disclosed in David, et al., U.S. Pat. No. 4,486,530, column 8, line 6 to column 15, line 63, incorporated herein by reference.

Another binding assay approach involves the luminescent immunoassay described in U.S. Ser. No. 07/704,569, filed May 22, 1991 entitled "Assay Method Utilizing Induced Luminescence", which disclosure is incorporated herein by reference.

As a matter of convenience, predetermined amounts of reagents employed in the present invention can be provided in a kit in packaged combination. A kit can comprise in packaged combination (a) a first oligonucleotide having the characteristic that, when reversibly hybridized to a portion of a polynucleotide to be detected, it is degraded under isothermal conditions by a 5'-nuclease to provide (i) a first fragment that is substantially non-hybridizable to the polynucleotide and (ii) a second fragment that is 3' of the first fragment and is substantially hybridizable to the polynucleotide, (b) a second oligonucleotide having the characteristic of at least a portion thereof hybridizing to a site on the polynucleotide that is 3' of the site at which the first oligonucleotide hybridizes wherein the polynucleotide is substantially fully hybridized to such portion of the second oligonucleotide under isothermal conditions, and (c) the above 5'-nuclease. The kit can further comprise a single nucleoside triphosphate.

The above kits can further include members of a signal producing system and also various buffered media, some of which may contain one or more of the above reagents. The above kits can also include a written description of one or more of the methods in accordance with the present invention for detecting a polynucleotide analyte.

The relative amounts of the various reagents in the kits can be varied widely to provide for concentrations of the reagents which substantially optimize the reactions that need to occur during the present method and to further substantially optimize the sensitivity of any assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit.

EXAMPLES

The invention is demonstrated further by the following illustrative examples. Temperatures are in degrees centigrade (°C.) and parts and percentages are by weight, unless otherwise indicated.

EXAMPLE 1

A single stranded target DNA ($2 \times 10^8$ molecules) (M13mp19 from Gibco, BRL, Bethesda, Md.) (the "target DNA") was combined with a $5'^{32}$P-labeled oligonucleotide probe, Probe 1, (10 uM) (5'CGT-GGG-AAC-AAA-CGG-CGG-AT3' (SEQ ID NO:1) synthesized on a Pharmacia Gene Assembler (Pharmacia Biotech, Piscataway, N.J.), an unlabeled oligonucleotide, Probe 2, (1 uM) (5'TTC-ATC-AAC-ATT-AAA-TGT-GAG-CGA-GTA-ACA-ACC-CGT-CGG-ATT-CTC3' (SEQ ID NO:2) synthesized on a Pharmacia Gene Assembler (Pharmacia Biotech), and 7.5 units of AmpliTaq DNA polymerase (from Perkin-Elmer Corporation, Norwalk, N.J.) in 50 uL of buffer (10 mM Tris-HCl, pH 8.5 , 50 mM KCl, 7.5 mM $MgCl_2$, 100 uM dATP) Probe 1 was a 20-base oligonucleotide that was fully complementary to the target DNA and had a label on the 5'-nucleotide. Probe 2, the unlabeled probe, was designed to anneal to the target DNA 3' to, and contiguous with, the site at which the labeled probe annealed to the target DNA. The DATP was shown to enhance the rate of cleavage by the polymerase. However, good results were obtained in the absence of DATP.

The reaction mixture was incubated at 72° C. and accumulation of product, a mononucleotide, namely, $5'^{32}$P—C—OH, was determined by visualization using autoradiography following polyacrylamide gel electrophoresis. The fold of amplification was determined by liquid scintillation spectrometry of excised reaction products. A $10^5$ fold amplification was observed.

The above reaction protocol was repeated using, in place of Probe 1, a labeled probe, Probe 3, (5'TCG-TGG-GAA-CAA-ACG-GCG-GAT3' (SEQ ID NO:3) prepared using a Pharmacia Gene Assembler) that had 21 nucleotides with one base at the 5'-end that was not complementary, and did not hybridize with, the target DNA. The product of this reaction was a dinucleotide, namely, $5'^{32}$P—TC—OH, that represented a $10^5$-fold amplification.

The above reaction protocol was repeated with different temperatures and different concentrations of reagents. All of the reactions, including those mentioned above, were carried out for a period of 3 hours. The following table summarizes the reagents and reaction parameters and the results obtained during the optimization procedure.

| Probe | Probe (μM) | Target number | Taq (units) | Temp °C. | Conditions | Fold amplification |
|---|---|---|---|---|---|---|
| 1 | 1 | $10^{10}$ | 2.5 | 72 | buffer as described; 1.5 mM $MgCl_2$ | $8.8 \times 10^2$ |
|   | 1 | $10^9$ | ↓ | ↓ | ↓ | $1.8 \times 10^3$ |
|   | 1 | $10^8$ | ↓ | ↓ | ↓ | N.D.* |
|   | 1 | $10^9$ | 7.5 | ↓ | ↓ | $2.0 \times 10^3$ |
|   | 1 | $10^9$ | ↓ | ↓ | add dATP(100 μM) | $1.4 \times 10^3$ |
|   | 1 | $10^8$ | ↓ | ↓ | ↓ | $1.0 \times 10^4$ |
|   | 10 | $10^9$ | ↓ | ↓ | ↓ | $1.4 \times 10^4$ |
|   | 10 | $10^8$ | ↓ | ↓ | ↓ | $3.6 \times 10^4$ |
|   | 1 | $10^9$ | ↓ | ↓ | increase $MgCl^2$ (7.5 mM) | $9.7 \times 10^3$ |
|   | 1 | $10^8$ | ↓ | ↓ | ↓ | $1.2 \times 10^4$ |
|   | 1 | $10^9$ | ↓ | ↓ | ↓ | $9.3 \times 10^3$ |
|   | 1 | $10^8$ | ↓ | ↓ | ↓ | $2.8 \times 10^4$ |
|   | 1 | $10^7$ | ↓ | ↓ | ↓ | N.D.* |
|   | 10 | $10^9$ | ↓ | 74 | ↓ | $3.7 \times 10^4$ |
|   | 10 | $10^8$ | ↓ | ↓ | ↓ | $1.1 \times 10^5$ |
|   | 10 | $10^7$ | ↓ | ↓ | ↓ | N.D.* |
| 3 | 1 | $10^9$ | ↓ | 72 | ↓ | $9.9 \times 10^3$ |
|   | 1 | $10^8$ | ↓ | ↓ | ↓ | $2.6 \times 10^4$ |
|   | 1 | $10^7$ | ↓ | ↓ | ↓ | N.D* |
|   | 10 | $10^9$ | ↓ | 74 | ↓ | $4.6 \times 10^4$ |

-continued

| Probe | Probe (μM) | Target number | Taq (units) | Temp °C. | Conditions | Fold amplification |
|---|---|---|---|---|---|---|
| | 10 | $10^8$ | ↓ | ↓ | ↓ | $1.0 \times 10^5$ |
| | 10 | $10^7$ | ↓ | ↓ | ↓ | N.D* |

*N.D. = not detected

EXAMPLE 2

The reaction protocol described in Example 1 was repeated using the following probes in place of Probe 1 or Probe 3:

Probe 4: 5'TTA-TTT-CGT-GGG-AAC-AAA-CGG-CGG-AT3' (SEQ ID NO:4) (from Oligos Etc., Inc., Wilsonville, Oreg.). Probe 4 had 26 nucleotides with six nucleotides at its 5'-end that were not complementary, nor hybridizable with, the target DNA. Probe 4 was present in a concentration of 1 micromolar. The product of this reaction was an intact seven nucleotide fragment, namely, 5'$^{32}$P-TTATTTC-OH, that represented a $1.5 \times 10^4$-fold amplification.

Probe 5: 5'GAT-TAG-GAT-TAG-GAT-TAG-TCG-TGG-GAA-CAA-ACG-GCG-GAT3' (SEQ ID NO:5) was prepared using a Pharmacia Gene assembler and had 39 nucleotides with 19 nucleotides at its 5'-end that were not complementary and did not hybridize with the target DNA. The product of this reaction was an intact 20 nucleotide fragment, namely, 5'$^{32}$P-GAT-TAG-GAT-TAG-GAT-TAG-TC-OH (SEQ ID NO:6), that represented a $1.5 \times 10^4$-fold amplification.

In repeating the above reactions in the absence of Probe 2, product was observed but the intensity of the spot on the polyacrylamide gel was significantly less than in the presence of Probe 2. Similar results were also observed where a 1 nucleotide space existed between the 3'-end of Probe 2 and the second probe when both probes were hybridized to the target DNA.

EXAMPLE 3

The reaction protocol described in Example 1 was repeated using $2 \times 10^9$ target molecules and Probe 5 (see Example 2) at a concentration of 1 micromolar in place of Probe 1. The reactions were conducted for three hours at a temperature of 72° C. using one of six different DNA polymerases, namely, AmpliTaq DNA polymerase, Replitherm(TM) DNA polymerase (Epicentre), Tfl(TM) DNA polymerase (Epicentre), Ultra Therm(TM) DNA polymerase (Bio/Can Scientific), Thermalase Tbr(TM) DNA polymerase (Amresco) and Panozyme(TM) DNA polymerase. The product of the reaction was a 20-nucleotide fragment (see Example 2). The following is a summary of the results obtained.

| Enzyme | Fragment (picomoles) |
|---|---|
| AmpliTaq | 32 |
| Replitherm | 18 |
| Tfl | 5 |
| Ultra Therm | 27 |
| Tbr | 16 |
| Panozyme | 25 |

The above experiments demonstrate that detectable cleavage products were generated in a target-specific manner at a single temperature using enzymes having 5'-nuclease activity and a labeled oligonucleotide. The accumulation of product was enhanced by the presence of a second oligonucleotide that was longer than the first labeled oligonucleotide and that was annealed to the target polynucleotide sequence 3' of the site of hybridization of the first labeled oligonucleotide. The reactions were carried out at temperatures very close to the melting temperature (Tm) of the labeled oligonucleotide with the target polynucleotide sequence.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

What is claimed is:

1. A method for modifying an oligonucleotide, said method comprising incubating said oligonucleotide with a polynucleotide a single nucleoside triphosphate and a 5'-nuclease wherein at least a portion of said oligonucleotide is reversibly hybridized to said polynucleotide under isothermal conditions to form a complex, said isothermal conditions being at or near the melting temperature of said complex, wherein said oligonucleotide is present in an amount in excess of the amount of said polynucleotide and wherein said oligonucleotide, when said portion is hybridized to said polynucleotide, is cleaved by said 5'-nuclease to provide (i) a first fragment that is substantially non-hybridizable to said polynucleotide and includes no more than one nucleotide from the 5'-end of said portion and (ii) a second fragment that is 3' of said first fragment with reference to the intact oligonucleotide and is substantially hybridizable to said polynucleotide.

2. The method of claim 1 wherein the amounts of fragments that are formed are at least 100-fold larger than the amount of said polynucleotide.

3. The method of claim 1 wherein a second oligonucleotide is present during said incubating, said second oligonucleotide having the characteristic of hybridizing to a site on said polynucleotide that is 3' of the site at which said oligonucleotide is reversibly hybridized and of being substantially non-reversibly hybridized to said polynucleotide under said isothermal conditions.

4. The method of claim 3 wherein said second oligonucleotide hybridizes to said polynucleotide at a site contiguous with the site on said polynucleotide at which said first oligonucleotide reversibly hybridizes.

5. The method of claim 4 wherein the amounts of fragments that are formed are at least 100-fold larger than the amount of said polynucleotide.

6. A method for detecting a polynucleotide analyte, which comprises:

(a) reversibly hybridizing an oligonucleotide with a polynucleotide analyte in the presence of a single nucleoside triphosphate and a 5'-nuclease under isothermal conditions wherein said polynucleotide analyte serves as a recognition element to enable said 5'-nuclease to cleave said oligonucleotide to provide (i) a first fragment that is substantially non-hybridizable to said polynucleotide analyte and (ii) a second fragment that lies 3' of said first fragment in the intact oligonucleotide and is substantially hybridizable to said polynucleotide analyte wherein at least a 100-fold molar excess of said first fragment and/or said second fragment are obtained relative to the molar amount of said polynucleotide analyte, and (b) detecting the presence of said first fragment and/or said second fragment, the presence thereof indicating the presence of said polynucleotide analyte.

7. The method of claim 6 wherein at least one of said first fragment and said second fragment has a label.

8. The method of claim 6 wherein said first fragment includes no more than 1 nucleotide from the 5'-end of that portion of said oligonucleotide that hybridizes to said polynucleotide analyte.

9. The method of claim 6 wherein a second oligonucleotide is present during said reversible hybridizing, said second oligonucleotide having the characteristic of hybridizing to a site on said polynucleotide analyte that is 3' of the site at which said oligonucleotide hybridizes wherein said polynucleotide analyte is substantially fully hybridized to said second oligonucleotide under said isothermal conditions.

10. The method of claim 9 wherein said oligonucleotide hybridization sites are contiguous.

11. A method for detecting a polynucleotide analyte, said method comprising:

(a) providing in combination a medium suspected of containing said polynucleotide analyte, a molar excess, relative to the suspected concentration of said polynucleotide analyte, of a first oligonucleotide at least a portion of which is capable of reversibly hybridizing with said polynucleotide analyte under isothermal conditions to form a complex, said isothermal conditions being at or near the melting temperature of said complex, a 5'-nuclease, a single nucleoside triphosphate and a second oligonucleotide having the characteristic of hybridizing to a site on said polynucleotide analyte that is 3' of the site at which said first oligonucleotide hybridizes wherein said polynucleotide analyte is substantially fully hybridized to said second oligonucleotide under said isothermal conditions, (b) reversibly hybridizing under said isothermal conditions said polynucleotide analyte and said first oligonucleotide, wherein said first oligonucleotide, when hybridized to said polynucleotide analyte, is cleaved by said 5'-nuclease as a function of the presence of said polynucleotide analyte to provide, in at least a 100-fold molar excess of said polynucleotide analyte, (i) a first fragment that is substantially non-hybridizable to said polynucleotide analyte and (ii) a second fragment that is 3' of said first fragment in said first oligonucleotide and is substantially hybridizable to said polynucleotide analyte, and (c) detecting the presence of said first fragment and/or said second fragment, the presence thereof indicating the presence of said polynucleotide analyte.

12. The method of claim 11 wherein said first fragment and/or said second fragment has a label.

13. The method of claim 12 wherein said label is selected from the group consisting of a member of a specific binding pair, dyes, fluorescent molecules, chemiluminescers, coenzymes, enzyme substrates, radioactive groups and suspendible particles.

14. The method of claim 11 wherein said polynucleotide analyte is DNA.

15. The method of claim 11 wherein said first fragment includes no more than 1 nucleotide from the 5'-end of that portion of said first oligonucleotide that is capable of hybridizing to said polynucleotide analyte.

16. The method of claim 11 wherein said second oligonucleotide hybridizes to said polynucleotide at a site contiguous with the site on said polynucleotide at which said first oligonucleotide hybridizes.

17. A method for detecting a DNA analyte, said method comprising:
(a) providing in combination a medium suspected of containing said DNA analyte, a first oligonucleotide at least a portion of which is capable of reversibly hybridizing with said DNA analyte under isothermal conditions to form a complex, said isothermal conditions being at or near the melting temperature of said complex, a 5'-nuclease, a single nucleoside triphosphate and a second oligonucleotide having the characteristic of hybridizing to a site on said DNA analyte that is 3' of the site at which said first oligonucleotide hybridizes wherein said DNA analyte is substantially fully hybridized to said second oligonucleotide under said isothermal conditions,
(b) reversibly hybridizing said DNA analyte and said first oligonucleotide under said isothermal conditions, wherein said first oligonucleotide, when hybridized to said DNA analyte, is cleaved by said 5'-nuclease to (i) a first fragment that is substantially non-hybridizable to said DNA analyte and (ii) a second fragment that is 3' of said first fragment in said first oligonucleotide and is substantially hybridizable to said DNA analyte wherein at least a 100-fold molar excess, relative to said DNA analyte, of said first fragment and/or said second fragment is produced and
(c) detecting the presence of said first fragment and/or said second fragment, the presence thereof indicating the presence of said DNA analyte.

18. The method of claim 17 wherein said first oligonucleotide has a substituent that facilitates separation of said first fragment or said second fragment from said medium.

19. The method of claim 17 wherein first fragment and/or said second fragment has a label.

20. The method of claim 19 wherein said label is selected from the group consisting of a member of a specific binding pair, dyes, fluorescent molecules, chemiluminescers, coenzymes, enzyme substrates, radioactive groups and suspendible particles.

21. The method of claim 17 wherein said second oligonucleotide hybridizes to said DNA analyte at a site contiguous with the site on said polynucleotide at which said first oligonucleotide hybridizes.

22. The method of claim 17 wherein said first oligonucleotide and/or said second oligonucleotide is DNA.

23. A method for detecting a polynucleotide analyte, said method comprising:
(a) providing in combination a medium suspected of containing said polynucleotide analyte, a first DNA oligonucleotide at least a portion of which is capable of reversibly hybridizing with said polynucleotide analyte under isothermal conditions to form a complex, said isothermal conditions being at or near the melting temperature of said complex, a 5'-nuclease, a single nucleoside triphosphate and a second DNA oligonucleotide having the characteristic of hybridizing to a site on said polynucleotide analyte that is 3' of, and contiguous with, the site at which said first DNA oligonucleotide hybridizes wherein said polynucleotide analyte is substantially fully hybridized to said second DNA oligonucleotide under said isothermal conditions,
(b) reversibly hybridizing under said isothermal conditions said polynucleotide analyte and said first DNA oligonucleotide, wherein said first DNA oligonucleotide, when hybridized to said polynucleotide analyte, is cleaved by said 5'-nuclease as a function of the presence of said polynucleotide analyte to provide, in at least a 100-fold molar excess of said polynucleotide analyte, (i) a first fragment that is substantially non-hybridizable to said polynucleotide analyte and (ii) a second fragment that is 3' of said first fragment in said first DNA oligonucleotide and is substantially hybridizable to said polynucleotide analyte, and
(c) detecting the presence of said first fragment and/or said second fragment, the presence thereof indicating the presence of said polynucleotide analyte.

24. The method of claim 23 wherein said first fragment and/or said second fragment has a label.

25. The method of claim 24 wherein said label is selected from the group consisting of a member of a specific binding pair, dyes, fluorescent molecules, chemiluminescers, coenzymes, enzyme substrates, radioactive groups and suspendible particles.

26. The method of claim 23 wherein said polynucleotide analyte is DNA.

* * * * *

UNITED STATES PATENT AND TRADEMARK OFFICE
CERTIFICATE OF CORRECTION

PATENT NO : 5,792,614
DATED : August 11, 1998
INVENTOR(S) : Linda M. Western, et. al.

It is certified that errors appear in the above-identified patent and that said Letters Patent are hereby corrected as shown below:

Column 1, Line 2: Delete "08/268,169" and insert –08/363,169--.

Column 3, Line 33: Delete "In" and insert –in--.

Column 6, Line 49: Delete "Soore" and insert –Spore--.

Column 7, Line 9: Delete "asteraides" and insert –asteroides--.

Column 18, Line 63: Delete "OL'" and insert –OL$^{11}$--.

Column 22, Line 20: Delete "DATP" and insert –dATP--.

Column 22, Line 22: Delete "DATP" and insert –dATP--.

Signed and Sealed this

Eighth Day of May, 2001

Attest:

NICHOLAS P. GODICI

Attesting Officer

Acting Director of the United States Patent and Trademark Office